United States Patent
Liu et al.

(10) Patent No.: US 10,664,679 B2
(45) Date of Patent: May 26, 2020

(54) OPTICAL FINGERPRINT IDENTIFICATION DISPLAY SCREEN AND DISPLAY DEVICE

(71) Applicants: Boe Technology Group Co., Ltd., Beijing (CN); BEIJING BOE OPTOELECTRONICS TECHNOLOGY CO., LTD., Beijing (CN)

(72) Inventors: Wei Liu, Beijing (CN); Xue Dong, Beijing (CN); Xiaochuan Chen, Beijing (CN); Haisheng Wang, Beijing (CN); Xiaoliang Ding, Beijing (CN); Yingming Liu, Beijing (CN); Weijie Zhao, Beijing (CN); Shengji Yang, Beijing (CN); Changfeng Li, Beijing (CN); Pengpeng Wang, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 136 days.

(21) Appl. No.: 15/326,928

(22) PCT Filed: Sep. 5, 2016

(86) PCT No.: PCT/CN2016/098043
§ 371 (c)(1),
(2) Date: Jan. 17, 2017

(87) PCT Pub. No.: WO2017/118067
PCT Pub. Date: Jul. 13, 2017

(65) Prior Publication Data
US 2018/0211085 A1    Jul. 26, 2018

(30) Foreign Application Priority Data
Jan. 4, 2016  (CN) .......................... 2016 1 0004800

(51) Int. Cl.
*G06K 9/00*    (2006.01)
*G02F 1/133*   (2006.01)
(Continued)

(52) U.S. Cl.
CPC .......... *G06K 9/0004* (2013.01); *A61B 5/1172* (2013.01); *G02F 1/13306* (2013.01);
(Continued)

(58) Field of Classification Search
None
See application file for complete search history.

(56) References Cited

U.S. PATENT DOCUMENTS

2005/0077819 A1* 4/2005 Park ................... H01L 27/3244
313/504
2009/0159786 A1* 6/2009 Yang ..................... G06F 3/0412
250/227.29
(Continued)

FOREIGN PATENT DOCUMENTS

CN    101359369 A    2/2009
CN    101464580 A    6/2009
(Continued)

OTHER PUBLICATIONS

Li, Jun, et al. "Refractive indices of liquid crystals for display applications." Journal of Display Technology 1.1 (2005): 51.*
(Continued)

*Primary Examiner* — Vu Le
*Assistant Examiner* — Tracy Mangialaschi
(74) *Attorney, Agent, or Firm* — Calfee, Halter & Griswold LLP

(57) ABSTRACT

This disclosure relates to an optical fingerprint identification display screen and a display device. In this disclosure, a plurality of photosensitive elements for fingerprint identification is arranged on an array substrate, such that mesh (Continued)

regions of a mesh-like black matrix layer corresponds to the photosensitive elements. A plurality of light guide members at least covering each of the photosensitive elements is arranged between each photosensitive element and the counter substrate. Since the light guide members and the counter substrate are in contact with each other, light reflected from ridges and valleys of a fingerprint will enter the light guide members maximally after passing through the mesh regions of the black matrix layer, and then directly impinge on the photosensitive elements after refraction within the light guide members.

20 Claims, 2 Drawing Sheets

(51) Int. Cl.
| | |
|---|---|
| H01L 27/146 | (2006.01) |
| G02F 1/1333 | (2006.01) |
| G02F 1/1335 | (2006.01) |
| A61B 5/1172 | (2016.01) |
| G06F 3/041 | (2006.01) |
| G02F 1/1368 | (2006.01) |
| H01L 27/15 | (2006.01) |
| H01L 27/32 | (2006.01) |
| H01L 31/113 | (2006.01) |
| H01L 31/16 | (2006.01) |

(52) U.S. Cl.
CPC ...... *G06F 3/0412* (2013.01); *H01L 27/14623* (2013.01); *H01L 27/14625* (2013.01); *H01L 27/14678* (2013.01); *G02F 1/1368* (2013.01); *G02F 1/13338* (2013.01); *G02F 1/133512* (2013.01); *G02F 2001/13312* (2013.01); *G02F 2001/133331* (2013.01); *H01L 27/156* (2013.01); *H01L 27/3234* (2013.01); *H01L 27/3246* (2013.01); *H01L 27/3283* (2013.01); *H01L 31/1136* (2013.01); *H01L 31/16* (2013.01)

(56) References Cited

U.S. PATENT DOCUMENTS

| | | | | |
|---|---|---|---|---|
| 2010/0053118 | A1* | 3/2010 | Chen | G06F 1/1601 345/175 |
| 2010/0321341 | A1 | 12/2010 | Cho et al. | |
| 2012/0211644 | A1* | 8/2012 | Zheng | G01J 9/00 250/208.2 |
| 2013/0051635 | A1* | 2/2013 | Wu | G06K 9/00046 382/124 |
| 2015/0340351 | A1* | 11/2015 | Rossi | H01L 25/167 257/82 |
| 2016/0132712 | A1* | 5/2016 | Yang | G06K 9/0002 348/77 |
| 2016/0224819 | A1* | 8/2016 | Kim | G06K 9/0004 |
| 2017/0010496 | A1* | 1/2017 | Shim | G02F 1/13394 |
| 2017/0220844 | A1* | 8/2017 | Jones | G06K 9/0053 |
| 2017/0270337 | A1* | 9/2017 | Zhu | G01J 1/44 |
| 2018/0165498 | A1* | 6/2018 | Xie | G06K 9/0004 |
| 2018/0247100 | A1* | 8/2018 | Zhu | G06K 9/0004 |

FOREIGN PATENT DOCUMENTS

| | | | | |
|---|---|---|---|---|
| CN | 104423728 A | | 3/2015 | |
| CN | 105095883 A | | 11/2015 | |
| CN | 105678255 A | | 6/2016 | |
| WO | WO-2017045130 A1 | * | 3/2017 | ........... G06K 9/0004 |
| WO | WO 2017063119 A1 | * | 4/2017 | ............... G06K 9/00 |

OTHER PUBLICATIONS

Search Report for International Patent Application No. PCT/CN2016/098043 dated Oct. 27, 2016.
First Office Action for Chinese Patent Application No. 201610004800.X dated Oct. 30, 2017.

* cited by examiner

OPTICAL FINGERPRINT IDENTIFICATION DISPLAY SCREEN AND DISPLAY DEVICE

RELATED APPLICATIONS

The present application is the U.S. national phase entry of PCT/CN2016/098043, with an international filling date of Sep. 5, 2016, which claims the benefit of Chinese Patent Application No. 201610004800.X, filed on Jan. 4, 2016, the entire disclosures of which are incorporated herein by reference.

FIELD

This disclosure relates to the field of display technologies, and in particular to an optical fingerprint identification display screen and a display device.

BACKGROUND ART

In recent years, with rapid development of display technologies, mobile products with biological identification functions have gradually become part of people's life. Particularly, increasing importance has been attached to fingerprinting for its identity uniqueness. Press type and slide type fingerprint identification based on a silicon substrate process has now been integrated into various mobile products. Moreover, future research will also focus on fingerprint identification technologies in a display region.

FIG. 1 illustrates a schematic structural view for an optical fingerprint identification device arranged in a display substrate. Specifically, each fingerprinting device 001 consists of two thin film transistors, one of them being a switching transistor 002 for controlling switches, and the other being a photosensitive transistor 003 serving as a photo sensor. During scanning of a fingerprint, due to differences between ridges and valleys of the fingerprint, light impinging on the finger will be reflected differently such that the light intensity reaching the photosensitive transistor 003 varies, resulting in different photocurrent differences. Under a control of the switching transistor 002, each current difference of the photosensitive transistor 003 is read out sequentially, and thereby detection for ridges and valleys of the fingerprint can be achieved.

In specific implementation, because of interference from ambient light and incident light, in the above optical fingerprint identification device, light received by the photosensitive transistor 003 after being reflected back carries lots of useless information. This influences detection for fingerprint detection signals and leads to a low signal-noise ratio for signals of such an optical fingerprint identification detection structure. Thus, the detection accuracy is limited.

SUMMARY

To this end, embodiments of this disclosure provide an optical fingerprint identification display screen and a display device, for solving problems such as limited detection accuracy caused by lots of useless information carried in light received by a photosensitive transistor device in an existing optical fingerprint identification device after being reflected back.

Therefore, embodiments of this disclosure provide an optical fingerprint identification display screen. The optical fingerprint identification display screen comprises: a counter substrate and an array substrate which are arranged opposite one another; a plurality of photosensitive elements arranged on a side of the array substrate facing the counter substrate for fingerprint identification; a mesh-like black matrix layer arranged on a side of the array substrate facing the counter substrate or on a side of the counter substrate facing the array substrate, mesh regions of the mesh-like black matrix layer corresponding to the photosensitive elements; and a plurality of light guide members arranged between each of the photosensitive elements and the counter substrate and at least covering each of the photosensitive elements.

According to a possible implementation, in the display screen provided by embodiments of this disclosure, each of the photosensitive elements is encompassed in a fingerprint identification member. Furthermore, the fingerprint identification member is arranged on a side of the array substrate facing the counter substrate.

According to a possible implementation, in the display screen provided by embodiments of this disclosure, each of the photosensitive elements is arranged in a gap between pixels of the array substrate. A one-to-one correspondence exists between the mesh regions of the mesh-like black matrix layer and the photosensitive elements.

According to a possible implementation, in the display screen provided by embodiments of this disclosure, the photosensitive elements are evenly distributed in a gap between pixels of the array substrate.

According to a possible implementation, in the display screen provided by embodiments of this disclosure, the light guide members have a refractive index greater than that of each film between the light guide members and a surface of the counter substrate facing away from the light guide members, and greater than that of a film located in a same horizontal plane as the light guide members.

According to a possible implementation, in the display screen provided by embodiments of this disclosure, the display screen comprises a liquid crystal display screen, and the light guide members comprise transparent spacers which are in one-to-one correspondence to the photosensitive elements.

According to a possible implementation, in the display screen provided by embodiments of this disclosure, the spacers have a refractive index greater than that of liquid crystal molecules in the liquid crystal display screen, and greater than that of each film on the counter substrate.

According to a possible implementation, in the display screen provided by embodiments of this disclosure, the display screen comprises an electroluminescent display screen, and the light guide members comprise transparent pixel defining layers.

According to a possible implementation, in the display screen provided by embodiments of this disclosure, the pixel defining layers have a refractive index greater than that of each film within a light emitting device on the electroluminescent display screen, and greater than that of each film on the counter substrate.

According to a possible implementation, the display screen provided by embodiments of this disclosure further comprises: a protective cover plate arranged on a side of the counter substrate facing away from the array substrate. At least in a position corresponding to the mesh region of the mesh-like black matrix layer, a surface of the protective cover plate facing away from the counter substrate comprises a rough surface.

Embodiments of this disclosure further provide a display device. The display device comprises: the optical fingerprint identification display screen provided by the above embodiments of this disclosure.

Embodiments of this disclosure provide an optical fingerprint identification display screen and a display device. The optical fingerprint identification display screen comprises a counter substrate and an array substrate which are arranged opposite one another. A plurality of photosensitive elements is arranged on a side of the array substrate facing the counter substrate for fingerprint identification. Besides, a mesh-like black matrix layer is arranged on a side of the array substrate facing the counter substrate or on a side of the counter substrate facing the array substrate, wherein mesh regions of the mesh-like black matrix layer correspond to the photosensitive elements. Furthermore, a plurality of light guide members is arranged between each photosensitive element and the counter substrate and at least covers each photosensitive element. Since light guide members are added above the photosensitive elements, and the light guide members and the counter substrate are in contact with each other, light reflected from ridges and valleys of a fingerprint will enter the light guide members maximally after passing through mesh regions of the black matrix layer. Additionally, since the light guide members cover each photosensitive element, light will directly impinge onto the photosensitive elements after refraction within the light guide members. Thus, loss of ridge or valley light before reaching each photosensitive element is reduced. In addition, due to a reflection function of the light guide members and a blocking function of the black matrix layer, interference to the ridge or valley light from display light and ambient light as interference light is shielded. Furthermore, interference between the photosensitive elements is also avoided. Thereby, more accurate fingerprint detection is achieved and the accuracy of fingerprint identification is improved.

DETAILED DESCRIPTION OF EMBODIMENTS

Figure 1:
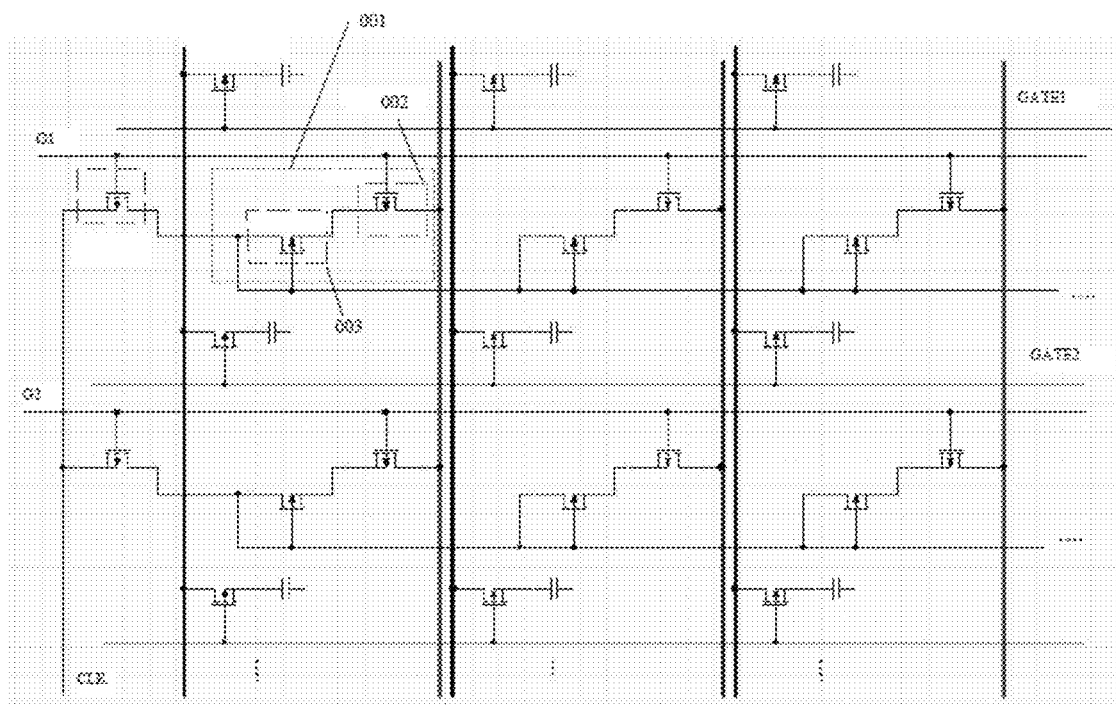
FIG. 1 is a schematic structural view for an optical fingerprint identification device in the prior art.

Specific implementations for the optical fingerprint identification display screen and the display device provided by embodiments of this disclosure will be illustrated as follows in detail with reference to the drawings.

Shapes and sizes of each component in the drawings are not provided to represent the true scale of the display screen, but only for the purpose of illustrating content of this disclosure.

Figure 2:
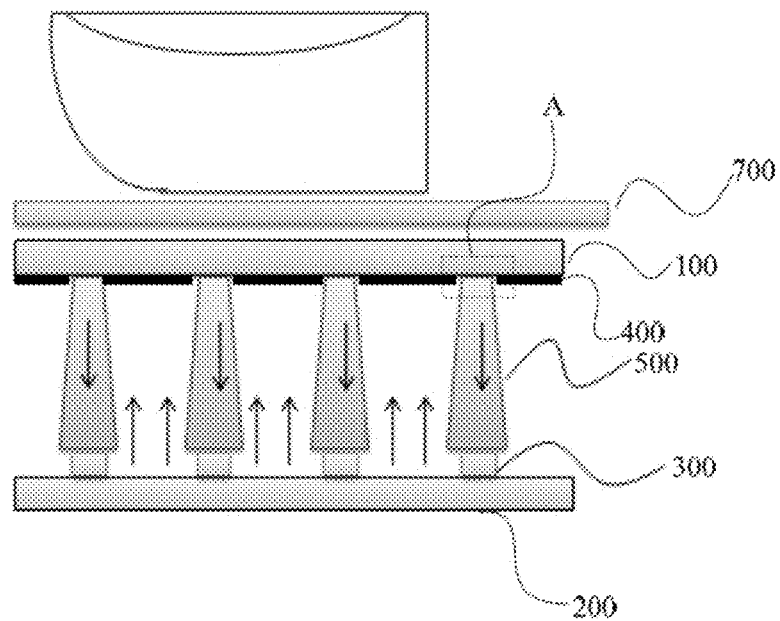
FIG. 2 is a schematic structural view for an optical fingerprint identification display screen provided by embodiments of this disclosure.

Embodiments of this disclosure provide an optical fingerprint identification display screen. As shown in FIG. 2, the display screen may comprise a counter substrate 100 and an array substrate 200 which are arranged opposite one another. Additionally, a plurality of photosensitive elements 300 can be arranged on a side of the array substrate 200 facing the counter substrate 100 for fingerprint identification. Additionally, a mesh-like black matrix layer 400 may also be arranged on a side of the array substrate 200 facing the counter substrate 100 or on a side of the counter substrate 100 facing the array substrate 200, wherein mesh regions A of the mesh-like black matrix layer 400 correspond to the photosensitive elements 300. In FIG. 2, as a specific example, the black matrix layer 400 is arranged on the counter substrate 100. Furthermore, a plurality of light guide members 500 is arranged between each of the photosensitive elements 300 and the counter substrate 100 and may at least cover each of the photosensitive elements 300. As a specific example, each of the photosensitive elements 300 can also be encompassed in a fingerprint identification member (not shown). In this case, the fingerprint identification member may be arranged on a side of the array substrate 200 facing the counter substrate 100.

In the display screen provided by the above embodiments of this disclosure, since light guide members 500 are added above the photosensitive elements 300, and the light guide members 500 and the counter substrate 100 are in contact with each other, light reflected from ridges and valleys of a fingerprint will enter the light guide members 500 maximally after passing through the mesh region A of the black matrix layer 400. Moreover, since the light guide members 500 cover each photosensitive element 300, light will directly impinge on the photosensitive elements 300 after being refracted within the light guide members 500. Thus, loss of ridge or valley light before reaching each photosensitive element 300 is reduced. In addition, due to a reflecting function of the light guide members 500 and a blocking function of the black matrix layer 400, interference to the ridge or valley light from display light and ambient light as interference light is shielded. Furthermore, interference between the photosensitive elements is also avoided. Thereby, more accurate fingerprint detection is achieved and the accuracy of fingerprint identification is improved.

According to a specific embodiment, in the display screen provided by the above embodiments of this disclosure, the fingerprint identification member for performing an optical fingerprint identification function can be specifically implemented in many different structures, which will not be limited here. Obviously, the photosensitive elements 300 arranged in the fingerprint identification member can be specifically implemented by photosensitive diodes, or other devices having photosensitive characteristics, which will not be limited here. Moreover, in the display screen provided by the above embodiments of this disclosure, the fingerprint identified by the fingerprint identification member can be specifically a fingerprint for a finger or other parts of an organism, such as a palm print. A print will fall within the protection scope of embodiments of this disclosure as long as it can represent the identity uniqueness for the organism.

Figure 3:
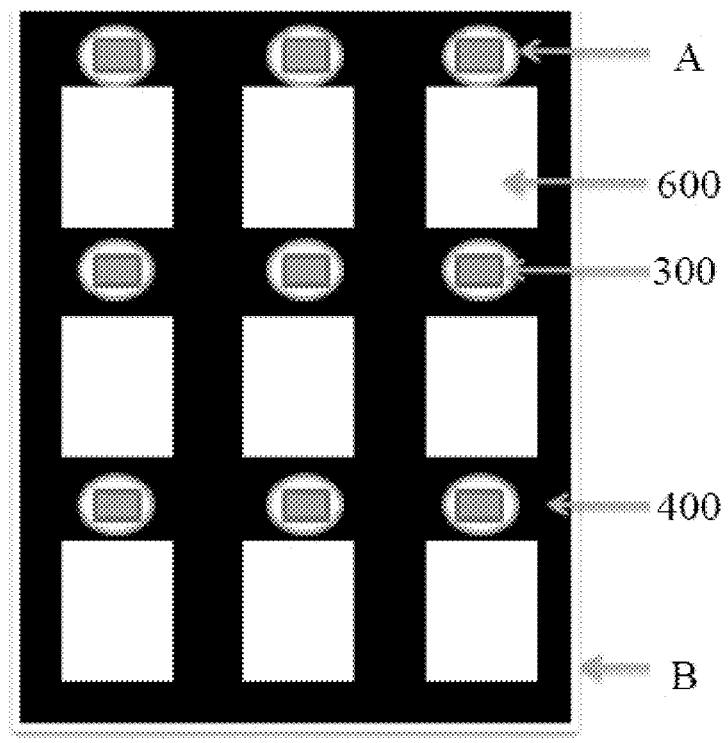
FIG. 3 is a schematic top view for an optical fingerprint identification display screen provided by embodiments of this disclosure.

According to a specific embodiment, in the display screen provided by the above embodiments of this disclosure, in order that the photosensitive elements 300 performing the fingerprint identification function do not occupy an aperture ratio of the display screen, the photosensitive elements 300 of each fingerprint identification member are generally arranged in a gap between pixels 600 of the array substrate 200, as shown in FIG. 3. In other words, the photosensitive elements 300 are arranged in an area of a display region B which would otherwise blocked by the black matrix layer 400. In this case, the black matrix layer 400 undergoes a drilling process to form mesh regions A which are in one-to-one correspondence to positions where the photosensitive elements 300 are located. By doing this, on one hand, light reflected from ridges and valleys of the fingerprint can enter the light guide members 500 after passing through the mesh region A. Meanwhile, on the other hand, the ambient light as interference light can be prevented from impinging on the light guide members 500 and the photosensitive elements 300, which improves the signal-noise ratio of each photosensitive element 300.

According to a specific embodiment, in order to facilitate detection and identification for a fingerprint, in the display screen provided by the above embodiments of this disclosure, the photosensitive elements 300 of each fingerprint identification member are evenly distributed in a gap between pixels 600 of the array substrate 200, as shown in FIG. 3.

Furthermore, in order that light reflected from ridges and valleys can enter the light guide members 500 maximally, microprocessing can be carried out at a position where the ridges and the valleys contact the display screen. By virtue of such a microprocess, light reflected from the ridges and the valleys can enter the light guide members 500 within the display screen to a larger extent. For example, generally, the display screen can further comprise a protective cover plate 700, which is arranged on a side of the counter substrate 100 facing away from the array substrate 200, as shown in FIG. 2. Moreover, at least in a position corresponding to the mesh region A of the black matrix layer 400, an outer surface (i.e., a surface facing away from the counter substrate 100) of the protective cover plate 700 can be microprocessed to form a rough surface.

Furthermore, in the display screen provided by the above embodiments of this disclosure, in order that loss of light reflected from ridges and valleys after entering the light guide members 500 can be reduced as far as possible, the law of refraction can be utilized when designing. In other words, when light enters an optically sparse medium to an optically dense medium, total reflection will occur if the incident angle satisfies a certain condition. Thus, regarding selection for a material of the light guide members 500, a refractive index of the light guide members 500 is chosen to be greater than that of each film between the light guide members 500 and an outer surface (i.e., a surface facing away from the light guide members 500) of the counter substrate 100, and greater than that of a film located in a same horizontal plane as the light guide members 500. Thereby, light reflected from ridges and valleys can be totally reflected in the light guide members 500, and meanwhile other interference light from the outside can be prevented from entering the light guide members 500. Thus, interference between lights reflected from ridges and valleys of the fingerprint is reduced.

According to a specific embodiment, the specific type of a display panel comprised in the display screen provided by the above embodiments of this disclosure will depend on and vary with implementations for the light guide members 500 arranged on the photosensitive elements 300.

Figure 4:
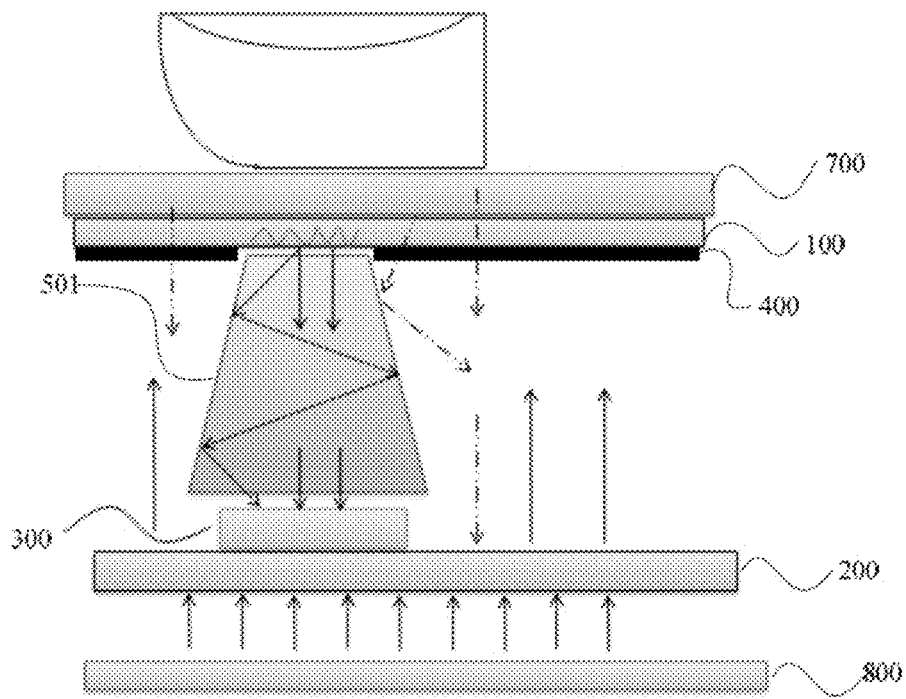
FIG. 4 is a schematic structural view for an optical fingerprint identification display screen provided by embodiments of this disclosure when comprising a liquid crystal display screen.

Specifically, when the display screen provided by the above embodiments of this disclosure is a liquid crystal display screen, spacers 501 are generally arranged between the array substrate 200 and the counter substrate 100. Therefore, part of the spacers 501 can be modified into transparent spacers 501 which are in one-to-one correspondence to the photosensitive elements 300. In this case, a refractive index of the spacers 501 can be greater than that of liquid crystal molecules, and greater than that of each film on the counter substrate 100. For example, a refractive index of the spacers 501 can be greater than that of a glass substrate, and that of an alignment layer. Moreover, in a specific embodiment, there are no special requirements for the shape of the spacers 501. Specifically, the spacers 501 can be erect cones, as shown in FIG. 4. Alternatively, the spacers 501 can be inverted cones, or even trapezoids, cuboids, or cubes. As shown in FIG. 4, orthographic projections of the spacers 501 on the array substrate 200 may cover the photosensitive elements 300. Generally, such orthographic projections can be slightly larger than the photosensitive elements. Specifically, as shown in FIG. 3, the photosensitive elements 300 are rectangular, and orthographic projections of the spacers 501 and the mesh region A of the black matrix layer 400 coincide as a circle.

As shown in FIG. 4, when performing fingerprint identification by a display screen, light is firstly emitted from a backlight 800, and blocked by the photosensitive elements 300 after passing through the array substrate 200. Thus, the light can only be transmitted upwards from a peripheral region thereof, and then pass through a liquid crystal cell and each film provided thereon thereby finally reaching a protective cover plate 700 of the display screen. When touch control is performed by a finger of a human body, light is reflected back into the liquid crystal cell with different intensities because of differences between ridges and valleys of a human finger. Due to microprocessing of the protective cover plate 700, light reflected from ridges and valleys of the fingerprint can enter the spacers from a window region (i.e., the mesh region) of the black matrix layer 400. Thus, linear propagation or total reflection propagation can be achieved. However, for other regions, light reflected from ridges and valleys rarely enters the spacers 501 due to a difference in the incident angle. Besides, it will be difficult for interference light to enter the spacers. Thus, interference between fingerprint information of each photosensitive element 300 and interference from other interference light to useful light to be acquired are reduced. Thereby, more accurate fingerprint detection is achieved and the accuracy of fingerprint identification is improved.

Specifically, when the display screen provided by the above embodiments of this disclosure is an electroluminescent display screen, pixel defining layers (PDL) are generally arranged between pixels of the array substrate 200. Therefore, part of the pixel defining layers can be modified into transparent pixel defining layers which are designed to cover the photosensitive elements 300. In this case, a refractive index of the pixel defining layers can be greater than that of each film within a light emitting device, and greater than that of each film on the counter substrate 100. For example, a refractive index of the pixel defining layers can be greater than that of a glass substrate, that of a cathode and that of a light emitting layer.

Based on a same disclosure concept, embodiments of this disclosure further provide a display device. The display device may comprise the optical fingerprint identification display screen provided by the above embodiments of this disclosure. The display device can be any product or component having a display function, such as a handset, a tablet computer, a television, a display, a notebook computer, a digital photo frame, a navigator and the like. For embodiments of the display device, the above embodiments of the optical fingerprint identification display screen can be referred to, which will not be repeated for simplicity.

Embodiments of this disclosure provide an optical fingerprint identification display screen and a display device. The optical fingerprint identification display screen comprises a counter substrate and an array substrate which are arranged opposite one another. A plurality of photosensitive elements is arranged on a side of the array substrate facing the counter substrate for fingerprint identification. Additionally, a mesh-like black matrix layer is arranged on a side of the array substrate facing the counter substrate or on a side of the counter substrate facing the array substrate, wherein mesh regions of the mesh-like black matrix layer correspond to the photosensitive elements. Furthermore, a plurality of light guide members is arranged between each photosensitive element and the counter substrate and at least cover each photosensitive element. Since light guide members are added above the photosensitive elements, and the light guide members and the counter substrate are in contact with each other, light reflected from ridges and valleys of the fingerprint will enter the light guide members maximally after passing through mesh regions of the black matrix layer. Additionally, since the light guide members cover each photosensitive element, light will directly impinge onto the photosensitive elements after being refracted within the light guide members. Thus, loss of ridge and valley light before reaching each photosensitive element is reduced. In addition, due to a reflecting function of the light guide members and a blocking function of the black matrix layer, interference to the ridge or valley light from display light and ambient light as interference light is shielded. Furthermore, interference between the photosensitive elements is also avoided. Thereby, more accurate fingerprint detection is achieved and the accuracy of fingerprint identification is improved.

Obviously, those skilled in the art can make various modifications and variations to this disclosure without deviating from the spirits and scopes of this disclosure. Thus, if these modifications and variations to this disclosure fall within the scopes of the present claims and the equivalent thereof, this disclosure is intended to include them too.

The invention claimed is:

1. An optical fingerprint identification display screen, comprising:
    a counter substrate and an array substrate arranged opposite one another;
    a plurality of photosensitive elements arranged on a side of the array substrate facing the counter substrate for fingerprint identification;
    a mesh-like black matrix layer arranged on the side of the array substrate facing the counter substrate or on a side of the counter substrate facing the array substrate, mesh regions of the mesh-like black matrix layer corresponding to the photosensitive elements; and
    a plurality of light guide members arranged between each of the photosensitive elements and the counter substrate and at least covering each of the photosensitive elements;
    wherein each mesh region of the mesh-like black matrix layer is located between two directly adjacent pixels in a column of pixels;
    and wherein each light guide member is a truncated cone comprising a top surface and a bottom surface, an area of the top surface is smaller than an area of the bottom surface, and the top surface is in contact with the counter substrate.

2. The display screen according to claim 1, wherein each of the photosensitive elements is encompassed in a fingerprint identification member, the fingerprint identification member being arranged on the side of the array substrate facing the counter substrate.

3. The display screen according to claim 1, wherein each of the photosensitive elements is arranged in a gap between pixels of the array substrate, and
    each mesh region of the mesh-like black matrix layer corresponds to one respective photosensitive element.

4. The display screen according to claim 3, wherein the photosensitive elements are evenly distributed in a gap between pixels of the array substrate.

5. The display screen according to claim 1, wherein the light guide members have a refractive index greater than that of each film between the light guide members and a surface of the counter substrate facing away from the light guide members, and greater than that of a film located in a same horizontal plane as the light guide members.

6. The display screen according to claim 5, wherein the display screen further comprises a liquid crystal display screen, and
    the light guide members comprise transparent spacers which are in one-to-one correspondence to the photosensitive elements.

7. The display screen according to claim 6, wherein the spacers have a refractive index greater than that of liquid crystal molecules in the liquid crystal display screen, and greater than that of each film on the counter substrate.

8. The display screen according to claim 5, wherein the display screen further comprises an electroluminescent display screen, and
    the light guide members comprise transparent pixel defining layers.

9. The display screen according to claim 8, wherein the pixel defining layers have a refractive index greater than that of each film within a light emitting device on the electroluminescent display screen, and greater than that of each film on the counter substrate.

10. The display screen according to claim 1, further comprising:
    a protective cover plate arranged on a side of the counter substrate facing away from the array substrate, wherein at least in a position corresponding to the mesh region of the mesh-like black matrix layer, a surface of the protective cover plate facing away from the counter substrate comprises a rough surface.

11. A display device, comprising: the optical fingerprint identification display screen according to claim 1.

12. The display screen according to claim 10, wherein each of the photosensitive elements is encompassed in a fingerprint identification member, the fingerprint identification member being arranged on the side of the array substrate facing the counter substrate.

13. The display screen according to claim 10, wherein each of the photosensitive elements is arranged in a gap between pixels of the array substrate, and
    there is a one-to-one correspondence between the mesh regions of the mesh-like black matrix layer and the photosensitive elements.

14. The display screen according to claim 13, wherein the photosensitive elements are evenly distributed in a gap between pixels of the array substrate.

15. The display screen according to claim 10, wherein the light guide members have a refractive index greater than that of each film between the light guide members and a surface of the counter substrate facing away from the light guide members, and greater than that of a film located in a same horizontal plane as the light guide members.

16. The display screen according to claim 15, wherein the display screen comprises a liquid crystal display screen, and
    the light guide members comprise transparent spacers which are in one-to-one correspondence to the photosensitive elements.

17. The display screen according to claim 15, wherein
the display screen comprises an electroluminescent display screen, and
the light guide members comprise transparent pixel defining layers.

18. The display device according to claim 11, wherein
each of the photosensitive elements is encompassed in a fingerprint identification member, the fingerprint identification member being arranged on the side of the array substrate facing the counter substrate.

19. The display device according to claim 11, wherein
each of the photosensitive elements is arranged in a gap between pixels of the array substrate, and
each mesh region of the mesh-like black matrix layer corresponds to one respective photosensitive element.

20. The display device according to claim 11, wherein the light guide members have a refractive index greater than that of each film between the light guide members and a surface of the counter substrate facing away from the light guide members, and greater than that of a film located in a same horizontal plane as the light guide members.

* * * * *